(12) United States Patent
Bryan

(10) Patent No.: US 10,130,378 B2
(45) Date of Patent: Nov. 20, 2018

(54) GENERATING PATIENT SPECIFIC INSTRUMENTS FOR USE AS SURGICAL AIDS

(75) Inventor: Jason A. Bryan, Avon Lake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 167 days.

(21) Appl. No.: 13/468,272

(22) Filed: May 10, 2012

(65) Prior Publication Data

US 2012/0290272 A1   Nov. 15, 2012

Related U.S. Application Data

(60) Provisional application No. 61/484,926, filed on May 11, 2011.

(51) Int. Cl.
| | |
|---|---|
| A61B 17/16 | (2006.01) |
| B33Y 80/00 | (2015.01) |
| A61B 34/10 | (2016.01) |

(52) U.S. Cl.
CPC .......... *A61B 17/1684* (2013.01); *A61B 34/10* (2016.02); *A61B 2034/102* (2016.02); *A61B 2034/108* (2016.02); *B33Y 80/00* (2014.12)

(58) Field of Classification Search
CPC ..... A61B 5/103; A61B 5/4528; A61B 5/4533; A61B 5/4824; A61B 5/6878; A61B 17/1684; A61B 34/10; A61B 2034/102; A61B 2034/108; A61F 2002/30945; A61F 2002/30955; A61F 2002/3096; A61F 2/38;
(Continued)

(56) References Cited

U.S. PATENT DOCUMENTS

| | | |
|---|---|---|
| 4,841,975 A | 6/1989 | Woolson |
| 5,098,383 A | 3/1992 | Hemmy et al. |

(Continued)

FOREIGN PATENT DOCUMENTS

| | | |
|---|---|---|
| AU | 2004293091 A1 | 6/2005 |
| AU | 2004293104 A1 | 6/2005 |

(Continued)

OTHER PUBLICATIONS

Hubbard, P.M, Constructive Solid Geometry for Triangulated Polyhedra, Dept fo Comp Science Brown University, Sep. 1, 1990.*

(Continued)

*Primary Examiner* — Brian S Cook
(74) *Attorney, Agent, or Firm* — Norton Rose Fulbright Canada LLP

(57) ABSTRACT

Systems and methods are provided for generating patient specific instruments for use as surgical guides. A region of interest within a body of a patient is scanned to provide a three-dimensional model of the region of interest. A first user is allowed to position a model of a selected implant with the three-dimensional model of the region of interest via a graphical user interface. A patient specific instrument model is generated from a generic patient specific instrument model according to the position of the model of the selected implant within the three-dimensional model of the region of interest and the position of at least one extension of the model that is not visible to the first user. A patient specific instrument is fabricated according to the patient specific instrument model.

24 Claims, 12 Drawing Sheets

(58) Field of Classification Search
CPC ... G06F 19/12; G06F 19/3437; G06F 19/3481
USPC .......... 600/407; 700/186; 606/88, 87, 88.87; 703/1, 2, 6; 345/419; 382/128; 701/6
See application file for complete search history.

(56) References Cited

U.S. PATENT DOCUMENTS

| | | | |
|---|---|---|---|
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 6,505,065 B1 * | 1/2003 | Yanof | A61N 5/103 600/103 |
| 6,754,556 B1 * | 6/2004 | Landers et al. | 700/182 |
| 6,757,582 B2 * | 6/2004 | Brisson et al. | 700/186 |
| 6,772,026 B2 | 8/2004 | Bradbury et al. | |
| 7,206,627 B2 * | 4/2007 | Abovitz et al. | 600/407 |
| 7,356,367 B2 * | 4/2008 | Liang et al. | 600/407 |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,630,750 B2 * | 12/2009 | Liang et al. | 600/407 |
| 7,634,119 B2 | 12/2009 | Tsougarakis et al. | |
| 7,717,956 B2 | 5/2010 | Lang | |
| 7,747,305 B2 * | 6/2010 | Dean et al. | 600/407 |
| 7,747,418 B2 | 6/2010 | Leu et al. | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 * | 1/2014 | Wong | A61B 17/1703 29/592 |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 8,974,459 B1 * | 3/2015 | Axelson, Jr. | A61B 17/155 606/86 R |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0171924 A1 * | 9/2004 | Mire et al. | 600/407 |
| 2004/0204644 A1 | 10/2004 | Tsougarakis et al. | |
| 2004/0204760 A1 | 10/2004 | Fitz et al. | |
| 2004/0225968 A1 * | 11/2004 | Look et al. | 715/778 |
| 2004/0236424 A1 | 11/2004 | Berez et al. | |
| 2005/0148843 A1 | 7/2005 | Roose | |
| 2005/0234461 A1 | 10/2005 | Burdulis et al. | |
| 2005/0267584 A1 | 12/2005 | Burdulis et al. | |
| 2006/0094951 A1 * | 5/2006 | Dean | A61F 2/30942 600/407 |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0248261 A1 * | 10/2007 | Zhou | G06F 19/321 382/154 |
| 2007/0250169 A1 | 10/2007 | Lang | |
| 2007/0288030 A1 * | 12/2007 | Metzger | A61B 17/154 606/87 |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0018546 A1 | 1/2009 | Daley | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 * | 4/2009 | Roose et al. | 606/87 |
| 2009/0099567 A1 | 4/2009 | Zajac | |
| 2009/0100368 A1 * | 4/2009 | Look et al. | 715/775 |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 * | 5/2009 | Park et al. | 606/88 |
| 2009/0157083 A1 | 6/2009 | Park et al. | |
| 2009/0222014 A1 | 9/2009 | Bojarksi et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0254367 A1 * | 10/2009 | Belcher | G06Q 50/22 705/2 |

(56) References Cited

U.S. PATENT DOCUMENTS

| | | |
|---|---|---|
| 2009/0270868 A1* | 10/2009 | Park et al. .................. 606/87 |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0121614 A1* | 5/2010 | Reghetti et al. .................. 703/1 |
| 2010/0138762 A1* | 6/2010 | Reghetti et al. .............. 715/765 |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0203478 A1 | 8/2010 | Rubbert |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0223032 A1* | 9/2010 | Reghetti et al. .................. 703/1 |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1* | 2/2011 | Bojarski ............. A61F 2/30942 623/20.35 |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1* | 3/2011 | Metzger et al. ................. 606/88 |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0087465 A1* | 4/2011 | Mahfouz ........................... 703/1 |
| 2011/0092977 A1 | 4/2011 | Salehi et al. |
| 2011/0093086 A1 | 4/2011 | Witt et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0190775 A1 | 8/2011 | Ure |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1* | 12/2011 | Bojarski ............. A61F 2/30942 623/20.35 |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0109591 A1* | 5/2012 | Thompson .............. G06F 17/50 703/1 |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018378 A1* | 1/2013 | Hananouchi ........ A61B 17/1739 606/87 |
| 2013/0018379 A1 | 1/2013 | Fitz et al. |
| 2013/0018380 A1 | 1/2013 | Fitz et al. |
| 2013/0018464 A1 | 1/2013 | Fitz et al. |

(56) References Cited

U.S. PATENT DOCUMENTS

| | | |
|---|---|---|
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0081400 A1* | 3/2014 | Azernikov et al. ........ 623/16.11 |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 2208470 A1 | 7/2010 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |

(56) References Cited

FOREIGN PATENT DOCUMENTS

| | | |
|---|---|---|
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | WO2009/076296 * | 12/2007 ............ A61B 17/74 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010/124164 A1 * | 10/2010 ............ A61B 17/58 |
| WO | 2010121147 A1 | 10/2010 |
| WO | WO-2010124164 A1 * | 10/2010 ......... A61B 17/1746 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Harper, I., How you see it . . . Now you don't! Object Visibility in AutoCAD 2011, Aug. 17, 2010 http://www.cadsoft-consult.com/blogs/acad/2010.*
Finkelstein, E., Easily hide and isolate objects in AutoCAD 2011, Apr. 25, 2010 http://www.ellenfinkelstein.com/acadblog/.*
Model, Websters II New Riverside University Dictionary, Houghton Mifflioon Company, 1994.*
Hidden_Definition, Webster's NewWorld Thesaurus, 1985 Simon & Schuster, Inc.*
HIPAA_2003 (Meeting HIPAA Requirements with Role-Based Access Control, Jul. 1, 2003 downloaded from https://hme-business.com/Articles/2003/07/01/Meeting-HIPAA-Requirements-with-RoleBased-Acces).*
RBAC_Surgery_Plan_2000 (Role-Based Access to Patient Clinical Data: The InterCar Approach in the Region of Crete, Proceedings of MIE 2000 and GMDS 2000, IOS Press, pp. 1074-1079, Hannover, Germany, Aug. 27-Sep. 1, 2000).*
Sandhu_1996 (Role-Based Access Control Methods, IEEE Computer, vol. 29, No. 2, Feb. 1996, pp. 38-47).*
Cera_2003 (Role-Based Viewing Envelopes for Information Protection in Collaborative Modeling, Drexel University Technical Report DU-CS-03-XX, Apr. 2003).*
PCT International Search Report and Written Opinion, dated Jul. 25, 2012, pp. 1-12.
Krekel, et al., Interactive Simulation and Comparative Visualisation of the . . . , Data Visualisation Group, Delft Univ. of Technology, pp. 1-13.
Krekel, et al., Combined Surface and Volume Processing for Fused Joint Segmentation, Springer Int'l. Journal of Computer Assisted Radiology and Surgery, pp. 1-24.
Krekel, et al., Visual Analysis of Multi-Joint Kinematic Data, Eurographics/IEEE-VGTC Symposium on Visulatization 2010, vol. 29 (2010), No. 3, pp. 1-10.
Krekel, et al., Evaluation of Bone Impingement Prediction in Preoperative Planning for Shoulder Arthroplasty, Proc. IMechE vol. 223, Part H: J.Engin. in Med., 2009, pp. 1-10.
Botha, et al., Pre-Operative Planning and Intra-Operative Guidance for Shoulder Replacement Surgery, Dagstuhl Publ., pp. 179-195.
Taylor et al, "Computer-Integrated Surgery, Technology and Clinical Applications", The MIT Press, Cambridge, MA, London, UK, pp. 451-463.

(56) References Cited

OTHER PUBLICATIONS

Hofmann et al, "Natural-Knee II System", Intermedics Orthopedics, Austin, TX, 1995.

* cited by examiner

GENERATING PATIENT SPECIFIC INSTRUMENTS FOR USE AS SURGICAL AIDS

CROSS-REFERENCE TO RELATED APPLICATION

This application claims the benefit of U.S. Provisional Patent Application No. 61/484,926, filed May 11, 2011, the entire contents of which are incorporated herein by reference.

TECHNICAL FIELD

The present invention relates to a preoperative planning system and, more particularly, to a system for generating patient specific instruments (PSIs) for use as surgical aids.

BACKGROUND OF THE INVENTION

For treatment of various problems with the shoulder, hip, or other body joint or bone (such as degenerative arthritis and/or traumatic injury), one method of providing relief to a patient is to replace the articulating surfaces with an artificial or prosthetic joint. In the case of a shoulder, the humerus and glenoid vault articulating surfaces are replaced. In the case of a hip, the femur and acetabulum articulating surfaces can be replaced. Both of these examples are of ball-and-socket type joints. Hinge-type joints, such as the knee or elbow, and static/fixed skeletal components, such as the long bones of the arm or leg, as well as interfaces such as those between spinal vertebrae and intervertebral discs, could also be subject to replacement and/or repair by the implantation of artificial or prosthetic components or other fixation devices related to the treatment of fractures, the sequelae of trauma, congenital pathology, or other issues causing a lack of ideal function. In such surgical procedures, pain relief, increased motion, and/or anatomic reconstruction of the joint are goals of the orthopedic surgeon. With multiple variations in human anatomy, prosthetic systems must be carefully designed, chosen, and implanted to accurately replicate the joints that they replace or the bone structures that they aim to change.

SUMMARY OF THE INVENTION

In accordance with a first aspect of the present invention, a non-transitory computer readable storing machine readable instructions is provided for generating a patient specific instrument (PSI) for use as a surgical guide. The machine readable instructions include a region modeling component configured to provide a three-dimensional model of a region of interest within a body from at least one imaging scan of the region of interest. A surgical planning component is configured to display a model of a selected implant and the three-dimensional model of the region of interest to a first user and allow the first user to position the model of the selected implant within the three-dimensional model of the region of interest. The model of the selected implant has at least one hidden attribute that is not visible to the first user. A PSI design component is configured to provide a patient specific instrument model from a generic PSI model according to the position of the model of the selected implant within the three-dimensional model of the region of interest and the at least one hidden attribute.

In accordance with another aspect of the present invention, a computer-implemented method is provided for generating a patient specific instrument (PSI) for use as a surgical guide. A region of interest within a body of a patient is scanned to provide a three-dimensional model of the region of interest. A first user is allowed to position a model of a selected implant with the three-dimensional model of the region of interest via a graphical user interface. A patient specific instrument model is generated from a generic PSI model according to the position of the model of the selected implant within the three-dimensional model of the region of interest and the position of at least one extension of the model that is not visible to the first user. The patient specific instrument is fabricated according to the patient specific instrument model.

In accordance with yet another aspect of the present invention, a system is provided for generating a patient specific instrument (PSI) for use as a surgical guide. The system includes a non-transitory computer readable medium storing machine readable instructions for performing a method, and a processor configured to execute the machine readable instructions. The method includes allowing a first user to position a model of a selected implant with the three-dimensional model of the region of interest, and allowing a second user to alter a first attribute of the model of the selected implant that is not visible to the first user. A patient specific instrument model is generated from a generic PSI model according to the positioning of the model of the selected implant by the first user, the alteration of the first attribute by the second user and a second attribute that is not visible to the first user or the second user.

BRIEF DESCRIPTION OF THE DRAWINGS

For a better understanding of the invention, reference may be made to the accompanying drawings, in which.

DESCRIPTION OF EMBODIMENTS

Figures 1, 3, 4:
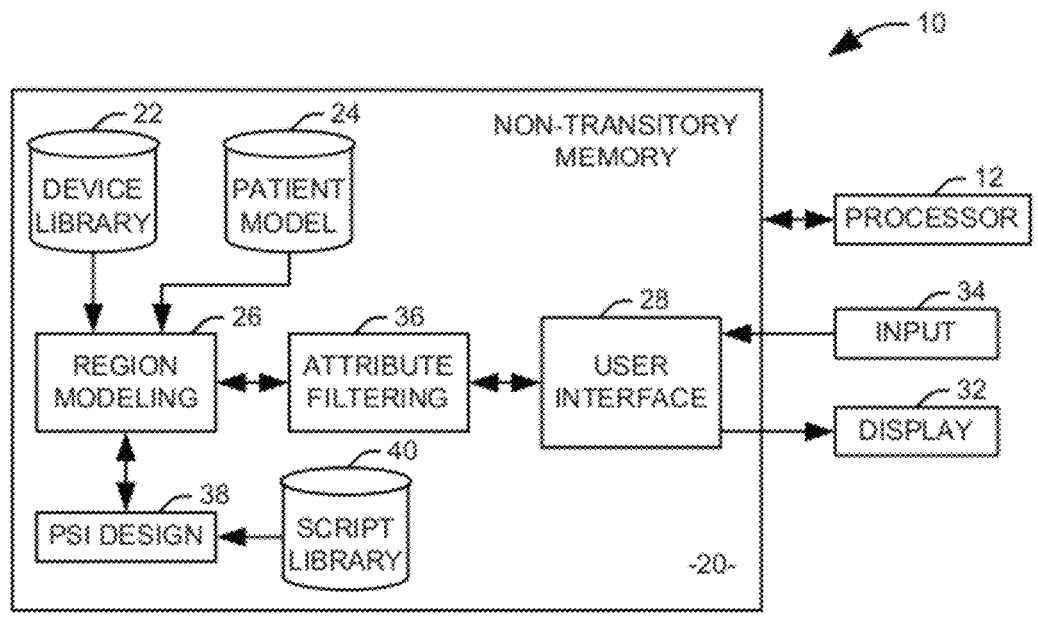
FIG. 1 illustrates a system for defining patient specific instrument assemblies in accordance with an aspect of the present invention.
FIG. 3 illustrates a first physical instantiation of a patient specific instrument model in accordance with an aspect of the present invention.
FIG. 4 illustrates a second physical instantiation of a patient specific instrument model in accordance with an aspect of the present invention.

A system in accordance with an aspect of the present invention is configured to allow a user, such as a surgeon, to place a simulated implant component into a model of a region of interest on a patient. It will be appreciated that the region of interest can comprises any region of a human or non-human patient's body in which it might be desirable to perform a surgical intervention. The model of the region of interest can include any form of tissue that might be of interest in conducting the surgical intervention. The patient model can be derived from a preoperative imaging procedure, such as a computed tomography (CT) scan, ultrasound imaging, a magnetic resonance imaging (MRI) procedure, a structured light, 3-D scan, a laser imaging procedure, or from a composite of multiple images derived from such scans, including stereographic composites. Some implants are an assembly of multiple interdependent pieces, and in these cases the implant assembly can be configured according to manufacturer specifications. The location and configuration of the implant in the virtual tissue can represent a preoperative surgical plan, allowing the user to customize the placement of the implant to the anatomy of the patient.

To this end, the system can extract a representation of the region of interest from the imaging data. A user can place a generic model, referred to as a "blank," onto a surface of the region of interest. If the blank has multiple pieces, those pieces can also be configured. The system can then create a single object from the blank and all its pieces in its current configuration and digitally subtract the surface of the region of interest from the object to create a unique "template" model that exactly fits the a contour of the tissue, such as a surface of a bone, in a single location. In another implementation, the blank can be generated directly from the region of interest by selecting a portion of the tissue surface and extruding it along the surface normal, or in another direction, to provide a model that fits the surface. The system can then augment the template, adding or subtracting features (e.g., bosses, holes, slots or platforms) according to the specification of the implant in order to create a "Patient Specific Instrument" model. It will be appreciated that some or all of these features can be produced from "hidden" attributes of the simulated implant component that are not visible to one or more users of the system, but interact with the object to create a template useful for guiding the surgical procedure. It will be appreciated that the hidden attributes of a given component can be inherent to the component, such that they are not added by any of the plurality of users. Some hidden attributes will be visible to and configurable by one or more users, but attributes can be hidden from all users. This PSI model can be manufactured using rapid prototyping technology to create a physical part. This part will fit on the patient bone in one specific location, allowing standard reusable instruments to use the PSI guiding structures, such as drill holes, guide holes for insertion of other structures, cutting slots, protrusions, bridges, and labels, as landmarks in order to prepare the bone so the selected implant can be placed according to the plan.

The term "stock" is used herein to indicate that the component indicated is not custom-manufactured or configured for the patient, but is instead provided as a standard inventory item by a manufacturer. A particular stock component may be selected automatically by the system or manually by the user from a product line range of available components, optionally with the user specifying a desired configuration, general or particular size (e.g., small, medium, large, or a specific measurement), material, or any other characteristic of the component. Indeed, the stock component could be manufactured only after the user has selected the desired options from the range of choices available. However, the stock component is differentiated from a custom-manufactured component in that the stock component is agnostic regarding a particular patient anatomy during the design and manufacturing processes for an instrument, prosthetic implant, or other component intended for that patient, while the patient anatomy is an input into at least one design and/or manufacturing process for a custom-manufactured component. The following description presumes the use of a stock prosthetic implant and stock instrument, though one of ordinary skill in the art will be able to provide for the use of the present invention with a custom-manufactured prosthetic implant or instrument, instead.

FIG. 1 illustrates a system 10 for defining patient specific instrument assemblies in accordance with an aspect of the present invention. The system includes a processor 12 and a non-transitory computer readable medium 20 configured to store data and machine readable instructions. It will be appreciated that by a "non-transitory computer readable medium," it is meant one or more physical computer readable media, local to the processor or connected via an appropriate bus or network connection, storing the data and instructions associated with the illustrated system 10. The non-transitory computer readable medium stores a device library 22 containing a plurality of device models representing potential devices for insertion into a region of interest on a patient or for use in performing the insertion of another device. It will be appreciated that each device model can be explicitly defined as a three-dimensional figure having defined boundaries within a local coordinate system or implicitly defined according to a generic model and a set of parameters defining a particular instance of the generic model. For example, a cylindrical device model might be stored as a set of parameters representing the radius, length, and number of sides for a generic cylinder model. In one implementation, each implant model is represented as a mesh object.

Imaging data representing the region of interest can be provided to the system from an external imaging device (not shown) and stored on the non-transitory computer readable medium as a patient model 24. Specifically, the patient model 24 can comprise a three-dimensional representation of one or more structures in the region of interest. In one implementation, the patient model can be an object representing a bone or joint of the patient.

A region modeling component 26 is configured to provide a three-dimensional representation of the region of interest, including at least a portion of the patient model 24 and device models from the device library 22. In accordance with an aspect of the present invention, a graphical user interface 28 is provided to allow a first user to view the device models and the patient model 24 at an associated display 32 and manipulate the position and orientation of at least one of the device models within the region of interest via an appropriate input device 34, such that the relative position and orientation of the at least one device model and the portion of the patient model 24 are altered. For example, the first user can review the portion of the patient model 24 and manipulate the position and orientation of the device model as to simulate the placement of an implant within the bone or joint represented by the patient model 24. In one embodiment, the first user can be a member of a surgical team responsible for implantation of the implant.

A given device model can have one or more attributes, that is, portions of the device model that do not directly correspond to the real-world device. Attributes can include extensions to the three-dimensional device model, apertures or depressions in the surface of the device model, additional models associated with the model, point locations, direction vectors, planes, labels, and categories. In accordance with an aspect of the invention, a model can include attributes that are not visible to one or more users, referred to as "hidden attributes". It will be appreciated that a hidden attribute of a model can be made selectively visible to users, such that an attribute can be visible to the first user but not to a second user. Some hidden attributes can be hidden from all users, for example, when adjustment of these attributes by a surgeon or technician would not be helpful. And, of course, some attributes can be visible to all users. To this end, an attribute filtering component 36 restricts the display of each model according to associated privileges of the user, such that the model displayed to the user contains no attributes hidden from the user.

In one implementation, the first user, generally a surgeon, can position the implant at a desired location with the model of the region of interest, and a second user, generally a technician, can manipulate one or more attributes associated with the implant and position a patient specific instrument (PSI) blank at a point within the region of interest suitable for placement of a physical patient specific instrument. It will be appreciated, however, that a "user" can also be an automated program for performing a particular function. Attributes can be hidden from an automated "user" simply by providing the automated system with a representation of the device model lacking the hidden attributes. For some applications, the attribute filtering component 36 can also work to prevent a given user from altering certain model attributes that are visible to the user. For example, the technician may be prohibited from altering one or both of the placement and orientation of an implant model placed by the surgeon even though the implant model is visible to the technician.

Once the PSI blank has been placed, the model is provided to a PSI design component 38 to generate a PSI for the implant. The PSI design component 38 can generate a model of the PSI from the PSI blank, the placement of the implant and its associated attributes, and the patient imaging data. In the illustrated implementation, the PSI blank is represented as a mesh object, and the PSI model can be formed through a series of geometry processing operations, on the patient imaging data, the implant and its various attributes, and the blank. It will be appreciated that the geometry processing operations can include Boolean operations between mesh objects, mesh "cleaning" operations, such as patching holes, removing extraneous disconnected surfaces, and similar processes, movement, scaling, rotation, or transformation (e.g., via a parameterized transform function) of objects or portions of objects, and creating a specific object from a parametric/implicit representation in a generic model. A series of geometry processing operations necessary to perform a discrete task (e.g., to create a blank having a desired shape and size, contour the blank to a portion of the patient's anatomy, etc.) can be stored as a script within a library of scripts 40. Accordingly, to produce a PSI model for a given implant, one or more scripts associated with the implant can be executed, representing the series of geometry processing operations necessary to produce a PSI specific to the patient's anatomy, the selected placement of the implant, and the placement of any structures auxiliary to the implant (e.g., guide pins, hex bosses, etc.). The resulting PSI model can be displayed to a user through the user interface 28 and saved in an appropriate format for use in fabricating the modeled PSI. In one implementation, the PSI model can be provided directly to a three-dimensional printer to produce the modeled implant.

In one implementation, the PSI blank can be a configurable mesh object, but it will be appreciated that the PSI blank can be implemented as an implicit model, such as a brep (boundary representation) or nurbs (non-uniform rational b-spline surface). Where the PSI blank is an implicit model, the PSI model can be created using brep objects, with the formation and combination of some of the brep objects would be determined by the hidden attributes and/or the script in a manner similar to the mesh model described above. Alternatively, the PSI model could be produced subdividing and "warping" a surface to conform to a specific shape, or generating a surface procedurally from the implicit model. In another implementation, the PSI blank can be generated dynamically by selecting and extruding a portion of the surface. In such a case, there is no need to then subtract the surface from the blank, because after extrusion, the surface-facing region is the same as the surface itself. This "surface-matched" blank would still be augmented with the attributes in a manner similar to the mesh model.

Figure 2:
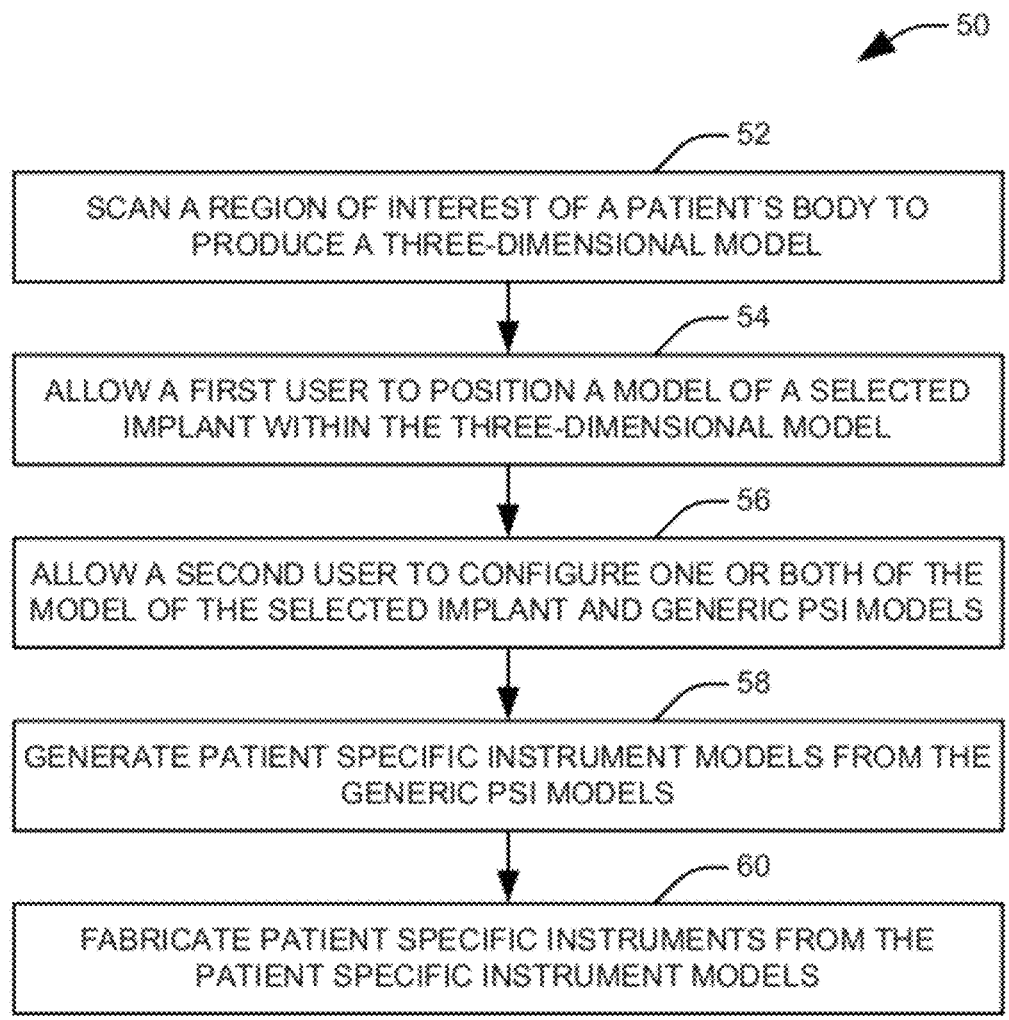
FIG. 2 illustrates a method for generating one or more patient specific instruments (PSIs) for use as surgical aids in the installation of a stock implant within a region of interest within a body of a patient.

FIG. 2 illustrates a method 50 for generating one or more patient specific instruments (PSIs) for use as surgical aids in the installation of a stock implant within a region of interest within a body of a patient. It will be appreciated that the illustrated method 50 can be implemented as machine executable instructions stored on one or more non-transitory computer readable media and executed by an associated processor. At 52, the region of interest is scanned to provide a three-dimensional model of the region of interest. One or more appropriate imaging modalities can be used to provide the scan data, and the scan data can be utilized to create the three-dimensional model as a model of the region of interest. The region of interest can be any portion of the body in which an implant device can be installed. For example, the region of interest can represent a shoulder joint or a hip joint of the patient.

At 54, a first user is allowed to position a model of a selected implant with the three-dimensional model of the region of interest. For example, the model of the selected implant can be displayed to the user via a graphical user interface, and the user can manipulate the position and orientation of the model using one or more input devices. In accordance with an aspect of the present invention, the model of the selected implant can have a number of associated attributes, including extensions to the three-dimensional device model, additional models associated with the model, point locations, direction vectors, planes, labels, and categories. Some of these attributes can be hidden from the first user, such that the display of the implant model to the first user includes only a first proper subset of the attributes associated with the model.

Once the implant model has been placed, a second user can configure one or both of the implant model and one or more generic patient specific instrument (PSI) models at 56. The display of the implant model to the second user can include a second proper subset of attributes, and the second user can be permitted to alter one or more of the displayed attributes. For example, the second user can configure one of the size and position of an extension of the model of the selected implant that was not visible to the first user. It will be appreciated that the attributes associated with a given implant model can include attributes visible to the first user but not visible to the second user, attributes visible to the second user, but not visible to the first user, attributes visible to both users, and attributes not visible to either user.

In one implementation, the second user can position and configure the one or more generic PSI models on the region of interest. As part of the configuration process, the second user can alter at least one of the size and the shape of each generic PSI model as well as the size and shape of any extensions from the model. In one implementation, the generic PSI model can include a cylindrical base portion and one or more extensions that can be rectangular or wedge-shaped. The second user can position the base portion, adjust its diameter and thickness, as well as determine an associated width, length, and shape of the extensions as part of the configuration process.

At 58, patient specific instrument models are generated from corresponding generic PSI models. For example, the PSI models can be generated according to the position of the generic PSI models, the position and orientation of the model of the selected implant within the three-dimensional model of the region of interest, and the position of at least one extension of the model that is not visible to the first user. In one implementation, each of the three-dimensional model, the generic PSI models, and the implant model can be represented as mesh models, and the patient specific instrument models can be created via a series of geometry processing operations. For example, each model can be represented by an associated script implementing a Constructive Solid Geometry (CSG) technique. The script language is designed to be easy to parse, as to make the language comprehensible to users without significant programming experience. It will be appreciated, however, that the script language herein is provided merely for the sake of example, and that other means for implementing the systems and methods described herein, including script languages having different grammars, can be utilized. For example, in one implementation, an implant model or generic PSI model can be implicitly defined according to one or more generic models and a set of parameters defining a specific instance of the generic model. The script can include comments, indicated by a double slash (//) to document the script and make it easier to understand the intent of each command, as well as arguments, indicated by dollar signs ($) representing mesh objects called from other locations by the script. Depending on the script, the mesh comprising each object can be used in operations and/or overwritten. Variables are mesh objects created local to the scope of script execution. They hold temporary meshes created by and used in operations. Models describe the location, relative to the root of the component assembly tree, of a specific model attribute, which is a mesh object. Some nodes in the tree have exactly one active "branch" at a time. For these nodes, a "?" in the path indicates that the currently active branch should be used when evaluating the remainder of the path. Functions allow a more complex operation to be applied to a mesh object, such as an argument, variable or model. One example is a smoothing operation. An associated argument is passed to the function to control its behavior. Another example is a transform function that can be applied to all or a selected portion of the geometry of the PSI model to produce a desired deformation in the PSI model. Finally, union (+), difference (−), and intersection (&) operators are used to combine two mesh objects via a Boolean operation. Table 1 describes the grammar of the scripting language in more detail.

TABLE 1

```
program    :=> [command]*
command    :=> lhs '=' rhs ';'
rhs        :=> operation | function | operand
lhs        :=> variable | argument
operation  :=> operand operator operand
operator   :=> '+' | '&' | '−'
function   :=> func '(' operand ',' arg ')'
operand    :=> '[' model_ref ']' | variable | argument
func       :=> split WHERE arg IS (largest|smallest) | smooth
WHERE arg IS float | save WHERE arg IS filename
variable   :=> name
argument   :=> '$'name
name       :=> (alpha)[alphanum]*
label      :=> (alphanum | ' ')*
alpha      :=> '_' | 'a' | 'b' | ... | 'z' | 'A' | 'B' | ... | 'Z'
num        :=> '0' | '1' | ... | '9'
alphanum   :=> alpha | num
float      :=> [num]* '.' [num]*
model_ref  :=> model_path | '@'model_label
model_path :=> (alphanum | ' ')* ['/' ( '?' | (alphanum | ' ')* ) ]*
model_label :=> '"label"'
filename   :=> "a valid system filename"
```

The final model for each patient specific instrument can be created by performing a series of geometry processing operations on the model of the selected implant, the at least one extension of the model, the three-dimensional model of the region of interest, and the generic PSI model as defined by a script associated with each implant model. In this way, the same generic PSI model can be used to create PSIs for multiple implant choices, with each implant defining how to make the final patient specific instrument model from the blank.

A number of features can be added to a given generic PSI model through these geometry processing operations. For example, one operation can comprise subtracting a portion of intersection between the three-dimensional model of the region of interest and the generic PSI model from the generic PSI model such that a first surface of the generic PSI model is contoured to a portion of a surface of the three-dimensional model of the region of interest. Similarly, a portion of intersection between an extension of the model and the generic PSI model from the generic PSI model can be subtracted from the generic PSI model as to form at least one guide structure in the generic PSI model. For example, the guide structure can represent an aperture or protrusion on the PSI model for maintaining one of an instrument and an implant in a desired orientation relative to the region of interest. Accordingly, each implant model can have its own built in guide extensions, for example, for its own placement or for guiding an associated instrument, hidden from the first user during placement of the implant, that define the positions of the guide structure in the patient specific instrument according to the first user's placement of the implant model.

Another operation can include taking the union of an extension of the model and the generic PSI model as to add a cylindrical bushing represented by the first extension to the generic PSI model. For example, the implant model can include an associated guide pin, and the cylindrical bushing can represent a hidden attribute of the model at the guide pin, such that placement of the guide pin by the first user can define the position of the bushing. The bushing can provide guidance for a drilling operation for placing the guide pin, while also minimizing lateral movement of the drill. For patient specific instruments in which the bone contour is not available for a guide, such as those intended to rest on the surface of a given stock implant, the guide pin can have hidden attribute representing a notched guide bar for orienting the patient specific implement relative to the guide pin, and the series of mesh operations can include taking the union of the guide bar and the generic PSI model as to add the guide bar to the generic PSI model. Table 2 shows one example of a script for making two patient specific instrument models from two generic PSI models, $blank and $locator. It will be appreciated that these examples are given merely as illustrations, and that the hidden attributes and associated geometry processing operations associated with a given implant procedure will vary with the position within the body, the type of implant, and the requirements of a particular surgical procedure. It will be further appreciated that the script could contain further instructions to add details such as engraved or embossed text, or further refine or process the mesh object.

TABLE 2

```
// create glenoid PSI model
drill_holes = [GlenoidImplant/Center Hex/bore/bore shape] +
[GlenoidImplant/Auxiliary Pin Assembly/?/rotation/Auxiliary
Pin/bore shape];
hex_boss = [GlenoidImplant/Center Hex/hex model] +
[GlenoidImplant/Auxiliary Pin Assembly/?/rotation/Auxiliary
Hex/hex model];
$template = $blank + hex_boss;
$template = $template − drill_holes;
$template = $template − $surface;
$template = split( $template, largest );
// create implant PSI model (locating guide)
drill_holes = [GlenoidImplant/Anterior Screw/bore/bore shape] +
[GlenoidImplant/Inferior Screw/bore/bore shape];
drill_holes = drill_holes + [GlenoidImplant/Posterior
Screw/bore/bore shape];
drill_holes = drill_holes + [GlenoidImplant/Auxiliary
Screw/bore/bore shape];
drill_holes = drill_holes + [GlenoidImplant/Auxiliary Pin
Assembly/?/rotation/Auxiliary Pin/guide wire bore shape];
$locator = [GlenoidImplant/drill guide/implant_guide_blank] +
[GlenoidImplant/Arm/Arm model];
$locator = $locator − drill_holes;
```

At 60, a patient specific instrument is fabricated according to each patient specific instrument model. The patient specific instrument may be made by any suitable method such as, but not limited to, selective laser sintering ("SLS"), fused deposition modeling ("FDM"), stereolithography ("SLA"), laminated object manufacturing ("LOM"), electron beam melting ("EBM"), three-dimensional printing ("3DP"), contour milling from a suitable material, computer numeric control ("CNC"), other rapid prototyping methods, or any other desired manufacturing process.

FIG. 3 illustrates a physical instantiation 70 of a glenoid template model created by the script of Table 2. The model includes a first drill guide 72 indicating a desired location for a center pin associated with an implant, and a second drill guide 74 indicating a desired location for an auxiliary pin associated with an implant. It will be appreciated that components commonly utilized in combination with a given implant can be included in the model of the implant to facilitate configuration of auxiliary components. One surface of the glenoid template 70 can be contoured to mate with a surface of a bone of a patient, allowing the drill guides 72 and 74 to be positioned correctly when the template is mounted to an appropriate location on the bone.

FIG. 4 illustrates a physical instantiation 80 of a metaglene guide model created by the script of Table 2. The illustrated metaglene guide 80 is configured to fit into an off-the-shelf implant to guide the placement of the implant. The guide 80 includes a plurality of holes 82-85 for dictating the position and trajectory of screws used to fasten the implant to the bone. Accordingly, when the guide 80 is positioned properly on its associated implant, any screws inserted through the holes 82-85 will be positioned as planned by a user, such as a surgeon, during generation of the guide model. Since the metaglene guide 80 does not directly mate with the bone surface, a guide bar 90 is included to allow for proper orientation of the device. A notch 92 in the guide bar is configured to engage with an auxiliary pin placed using the glenoid template of FIG. 3, such that when the notch is engaged with the auxiliary pin, the orientation of the metaglene guide is correct.

FIGS. 5-22 collectively illustrate the operation of a system in accordance with an aspect of the present invention. The application described herein is directed toward planning the surgical implantation of a prosthetic implant into the glenoid vault of the scapula, but it will be appreciated that the system can be used to plan any of a number of procedures, including, but not limited to, implants for use in hip joints, shoulder joints, knee joints, ankle joints, phalangeal joints, metatarsal joints, spinal structures, long bones (e.g., fracture sites), or any other suitable environment. For example, the implanted prosthetic device could be an internal fixation device (e.g., a bone plate), a structure of a replacement/prosthetic joint, or any other suitable artificial device to replace or augment a missing or impaired part of the body.

Figure 6:
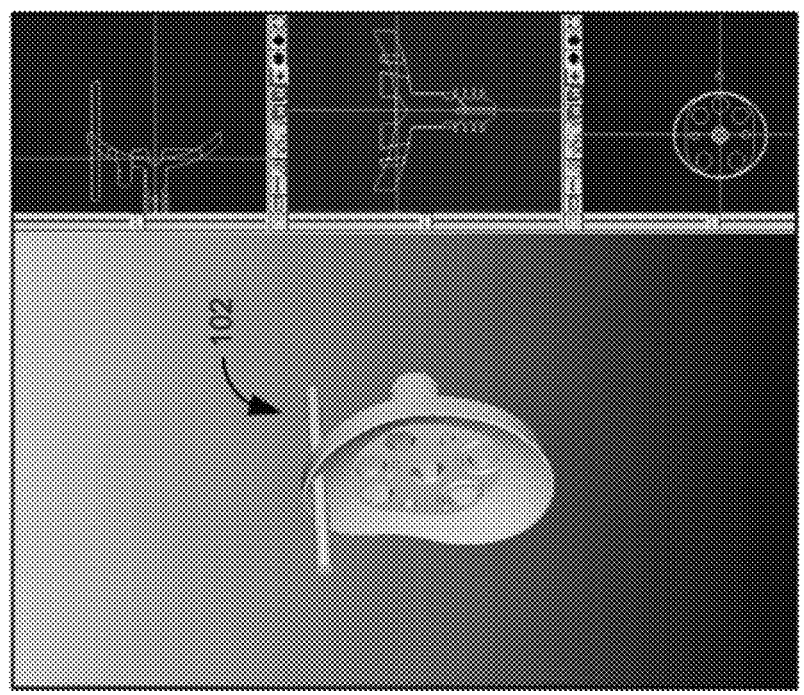
FIG. 6 illustrates an example of a device model for the prosthetic device illustrated in FIG. 5 as it might appear to a first user using a system in accordance with an aspect of the present invention.
Figure 5:
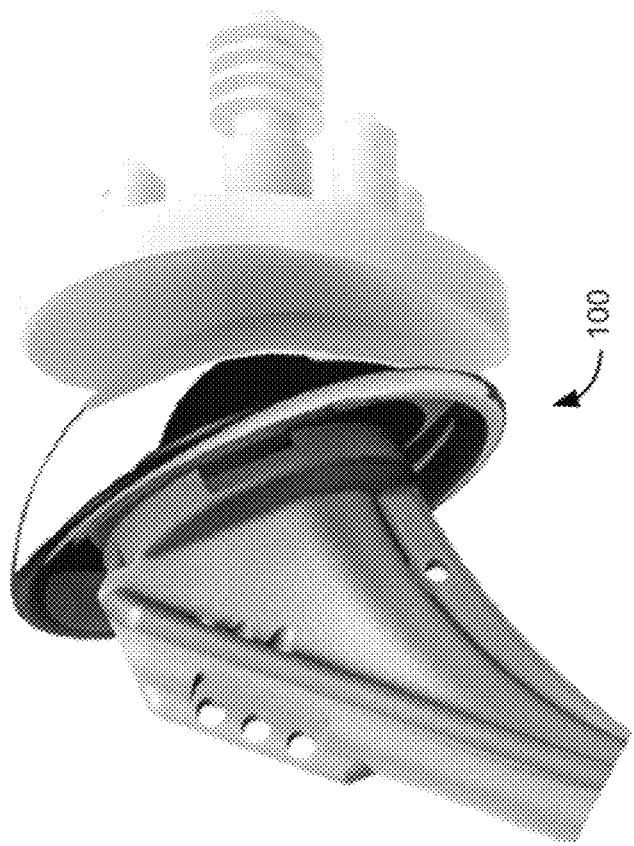
FIG. 5 illustrates one example of a prosthetic implant device.

To facilitate preoperative planning, a first user, such as a surgeon, can view the imaging data for a given patient, for example, as a three-dimensional model of a region of interest, and based upon knowledge of other patient characteristics (such as, but not limited to, height, weight, age, and activity level), choose a desired prosthetic device from a library of device models available for use in the surgical procedure. FIG. 5 illustrates one example of a prosthetic device 100, with the illustrated device 100 being configured for implantation into a scapula. Upon selection of the desired prosthetic device, a device model can be retrieved to represent the selected device and displayed to the first user. FIG. 6 illustrates an example of a device model 102 for the prosthetic device illustrated in FIG. 5 as it might appear to a first user, such as a surgeon, using a system in accordance with an aspect of the present invention.

The surgeon can place the device model 102 into a position and orientation relative to a model of a region of interest within a patient to simulate a final placement of a corresponding stock implant device after the surgical procedure. An orientation of a structure, as used herein, includes both the absolute location of the structure upon or with respect to another structure and the arrangement or positioning in space of the structure (e.g., rotation, pitch, yaw, camber, or any other placement-related variable of the structure). In practice, there may be some overlap or superposition between the device model 102 and the modeled tissue. This superposition is permissible in the virtual environment of the described system and may help to indicate areas of the patient's tissue which could be targeted for alteration during placement of the stock implant.

Figure 7:
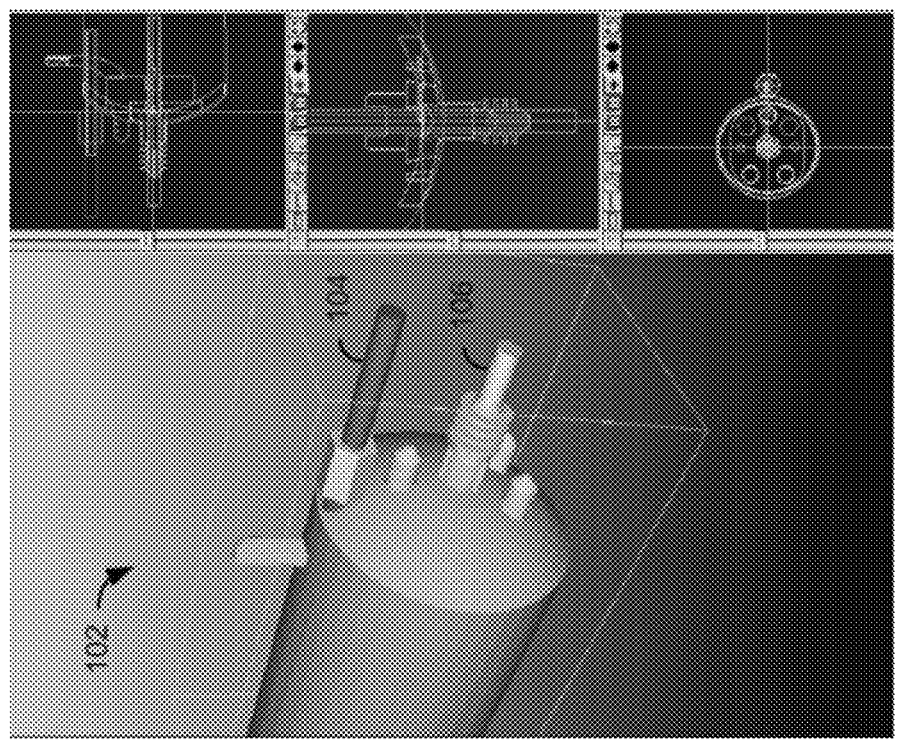
FIG. 7 illustrates the device model of FIG. 6 with all of its associated attributes shown.
Figure 8:
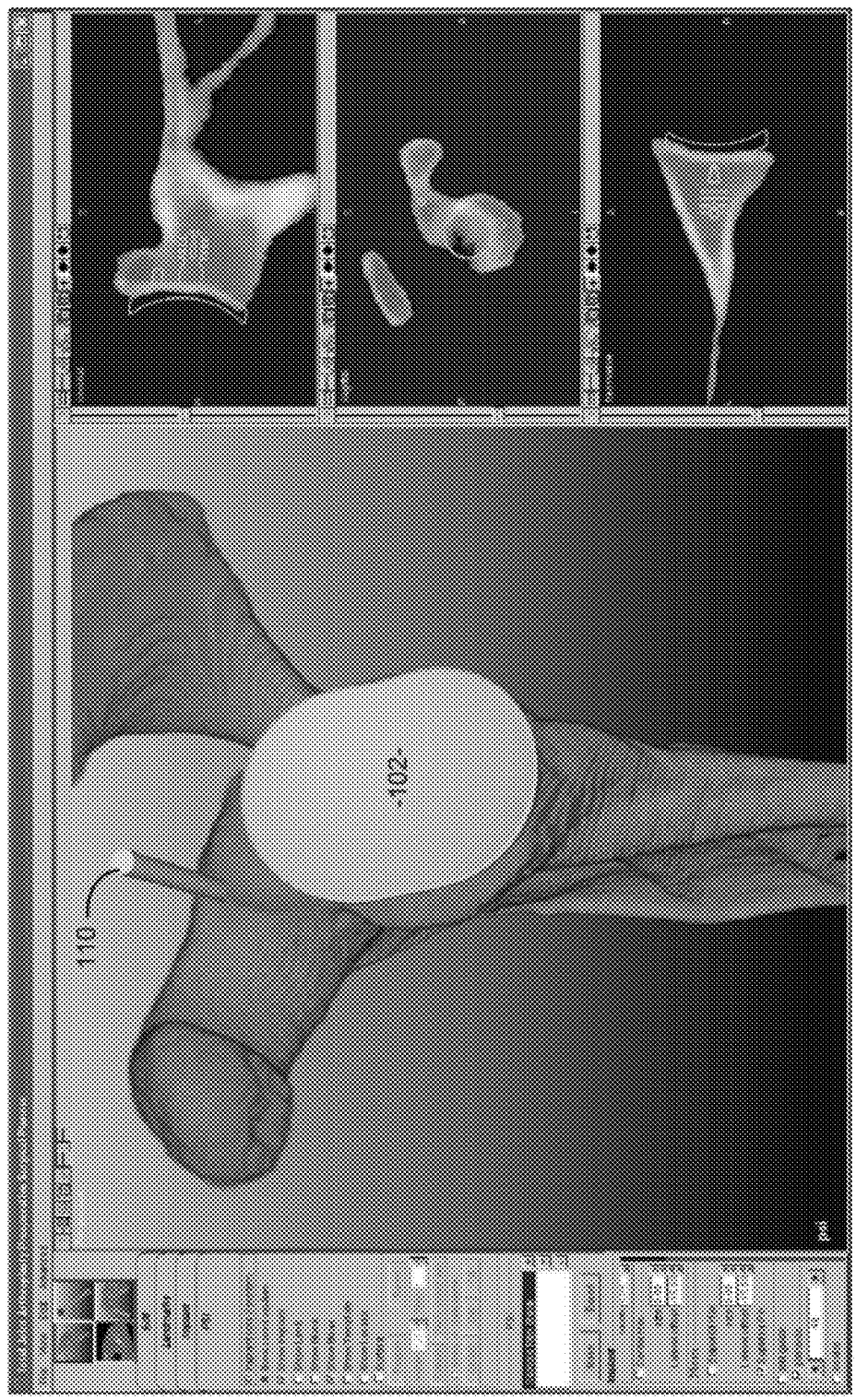
FIG. 8 illustrates the model of FIG. 6 overlaid on a model of a region of interest in a patient.

FIG. 7 illustrates the device model 102 of FIG. 6 with all of its associated attributes shown. For example, the device model 102 includes several cylinders 104 and 106 representing the position of drill holes within the bone of the patient that facilitate affixing the implant. The device model 102 is illustrated in FIG. 8 overlaid on a model of a region of interest in the patient, specifically, a portion of a patient's scapula. In FIG. 8, the device model 102 is depicted as the model would appear to a surgeon, such that many of the attributes shown in FIG. 7 are hidden. During such a simulation, the surgeon can adjust or reorient the position of the device model 102 with respect to the modeled region of interest, even to the extent of simulating the dynamic interaction between the two, as may be helpful to refine the selection, placement, and orientation of the selected prosthetic device for a desired patient outcome. It will be appreciated that, in the illustrated implementation, the guide pin 110 is visible, and that the surgeon can also select the placement of the guide pin relative to the implant 102.

In one implementation, the surgeon can also make changes to the model of the region of interest of the patient to facilitate placement of the implant. For example, native patient tissue could be drilled, planed, reamed or otherwise removed, or the native patient tissue could be built up using bone grafts or other substances.

Figure 9:
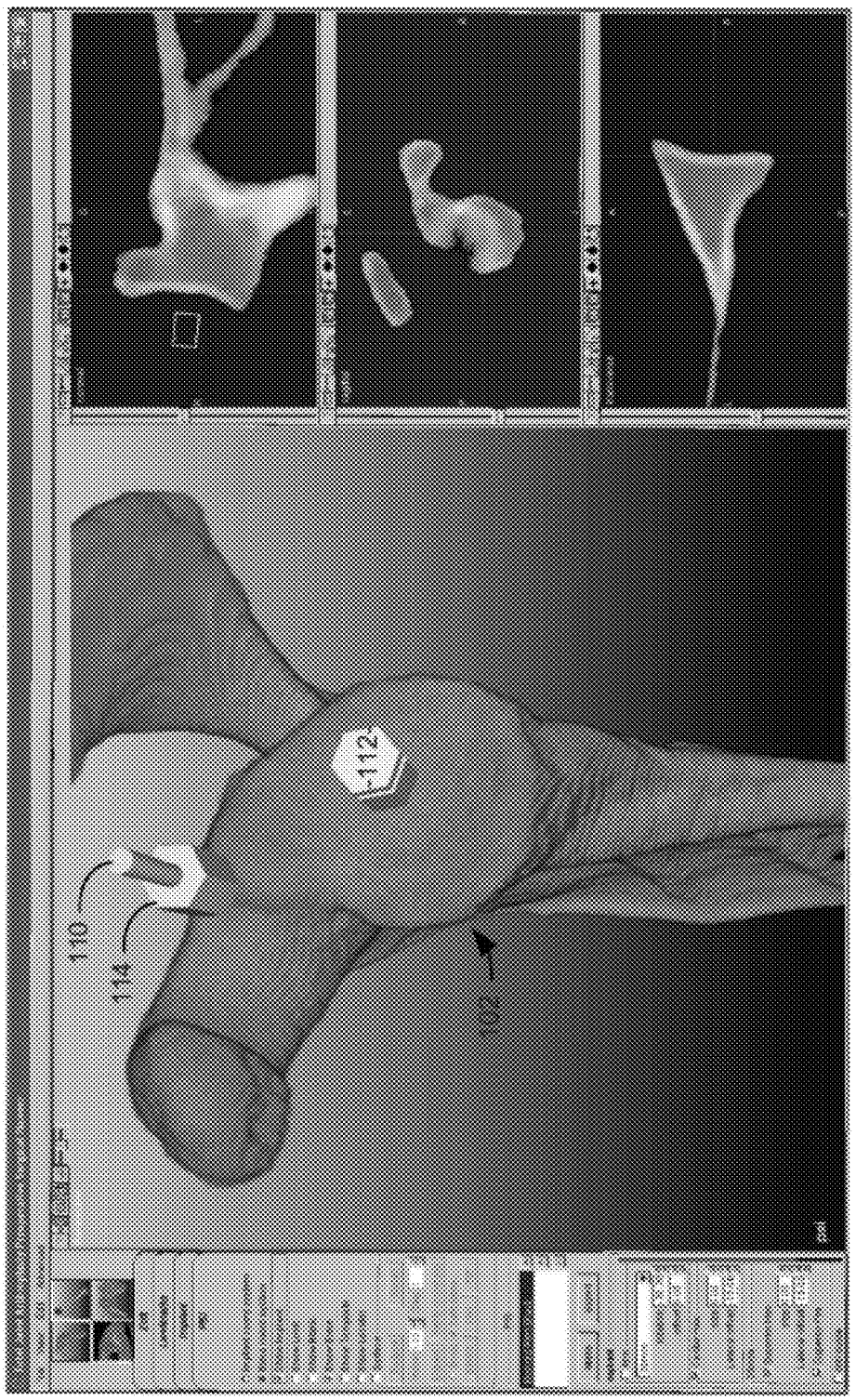
FIG. 9 illustrates the device model overlaid on the model of the patient's scapula as the device model would appear to a second user.

FIG. 9 illustrates the device model 102 overlaid on the model of the patient's scapula as the model would appear to a second user, specifically a technician, such that the displayed attributes are different from those shown in FIG. 8. In the illustrated implementation, the position and orientation of the device model 102 cannot be changed by the technician, but attributes hidden from the surgeon are displayed. For example, the device model 102 includes a first hex boss 112 attached to a center axis of the device model and a second hex boss 114 attached to the guide pin 110. The technician can translate and resize each hex boss 112 and 114 along their respective axes.

Figure 11:
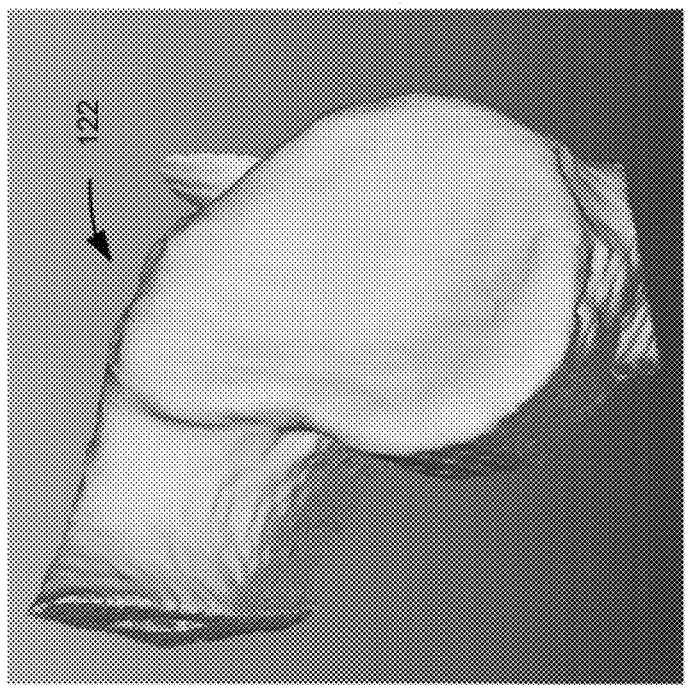
FIG. 11 illustrates a surface model of the region of interest created from the selected surface of FIG. 10.
Figure 10:
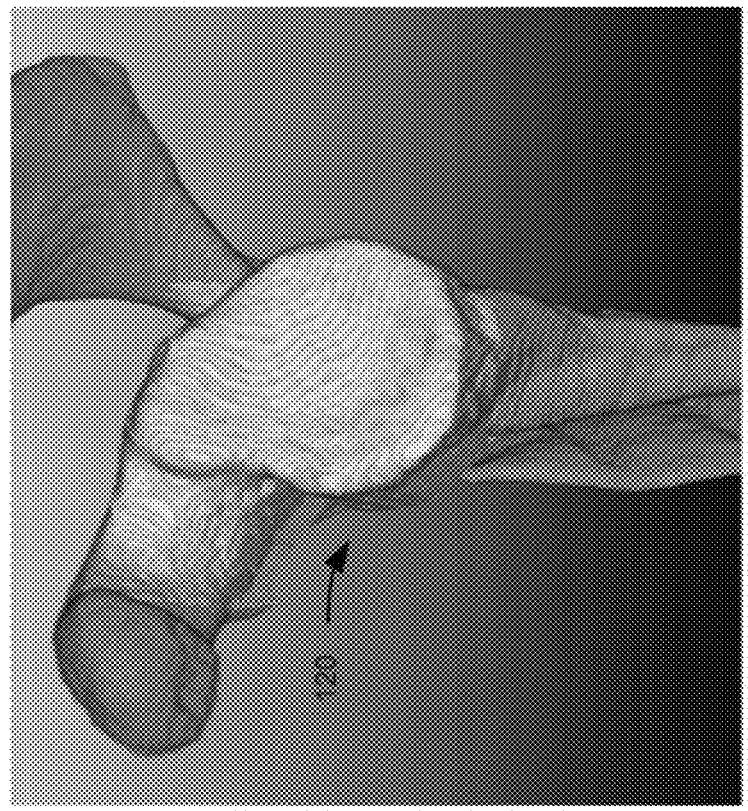
FIG. 10 illustrates a selection of a surface on a region of interest.

Once the surgeon and technician are satisfied with the placement of the device model 102 and its associated attributes, models representing one or more patient specific instruments (PSIs) for performing the implantation of the prosthetic are generated. One step in the PSI generation process is illustrated in FIGS. 10 and 11. In FIG. 10, a relevant portion 120 of a region of interest, specifically on the patient's scapula, is highlighted. For example, the relevant portion can be selected by the system in response to the positioning of the implant or selected manually by one of the surgeon and the technician. FIG. 11 illustrates the surface model 122 extracted from the relevant portion of the region of interest. The surface model 122 can comprise a mesh model of the relevant portion of the region of interest that represents the surface features of the region.

In one implementation, the surface model 122 can be altered to remove features that could interfere with the generation of a PSI model that would engage with the surface of the region of interest. For example, the system can remove "underhanging features," which are protuberances on or near a surface of the surface model that is intended to be in contact with the patient specific instrument that lack local support. In other words, underhanging features form gaps in the surface model structure beneath the surface intended to be in contact with the patient specific instrument. Avoiding underhanging features is desirable, because they can cause unnecessary extensions of a patient specific instrument that would prevent it from attaching it to the bone surface. Underhanging features can be removed, for example, by propagating the mesh of the surface model 122 in the direction of the implant axis to remove the gap formed by the underhanging feature. Other modifications can include filling/fixing holes and defects in the model, smoothing the model surface, and adding or removing material to a region of the surface model 122. In practice, any operation or filter that can alter the model, in whatever format the model is represented, can be used to create the surface model, and the specific method will vary with the implementation.

Figure 12:
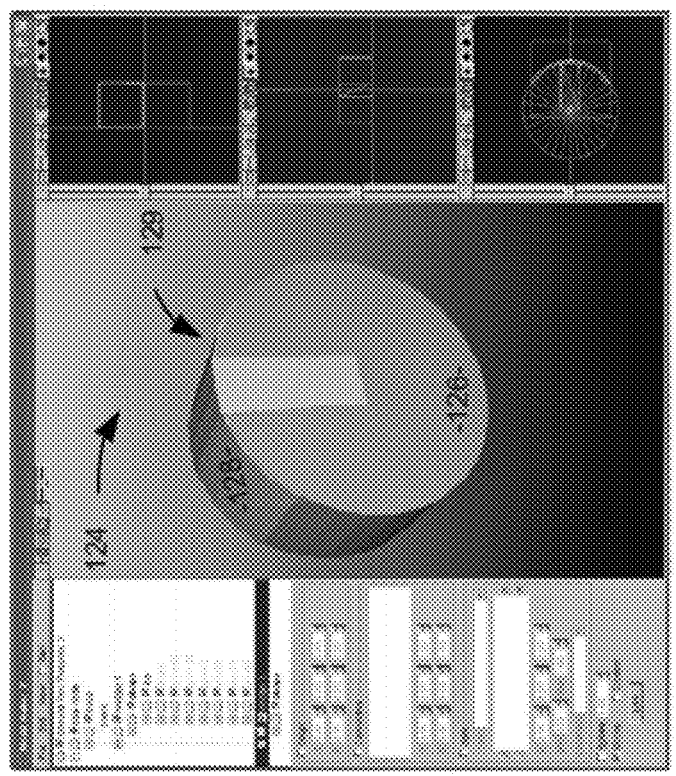
FIG. 12 illustrates one example of a generic PSI model in accordance with an aspect of the present invention.

Once the surface model has been created, a generic PSI model can be selected and positioned relative to the surface model of the region of interest. For example, the generic PSI model can be selected and placed by the system in response to the selection and placement of the device model or selected and placed by a technician. FIG. 12 illustrates one example of a generic PSI model 124 in accordance with an aspect of the present invention. The illustrated generic PSI model 124 is a model comprising a cylinder 126 and two "wedge" shapes 128 and 129. Each wedge 128 and 129 can be set to one of several predefined shapes, including a rectangular "bar" or a substantially triangular "pie" shape, or disabled such that it does not appear in the generic PSI model 124.

Figure 13:
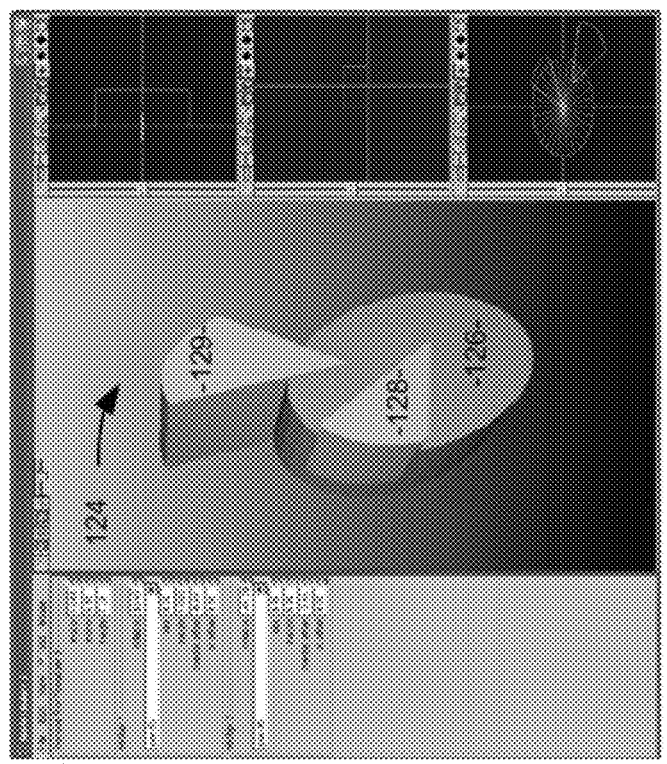
FIG. 13 illustrates the generic PSI model of FIG. 12 after configuration.

The generic PSI model 124 can be configured by the system or a technician at the time of creation. FIG. 13 illustrates the generic PSI model 124 after it has been configured. During configuration, the width of the cylinder 126 and the length of the cylinder along major and minor axes can be selected to adequately cover a desired portion of the region of interest. Similarly, the wedges 128-129 can be changed in shape (e.g., rectangular, "pie shaped", etc.), opening angle, position on the cylinder, length, width, or any other appropriate parameter to better match the generic PSI model 124 to an associated region of interest and device model.

Figure 14:
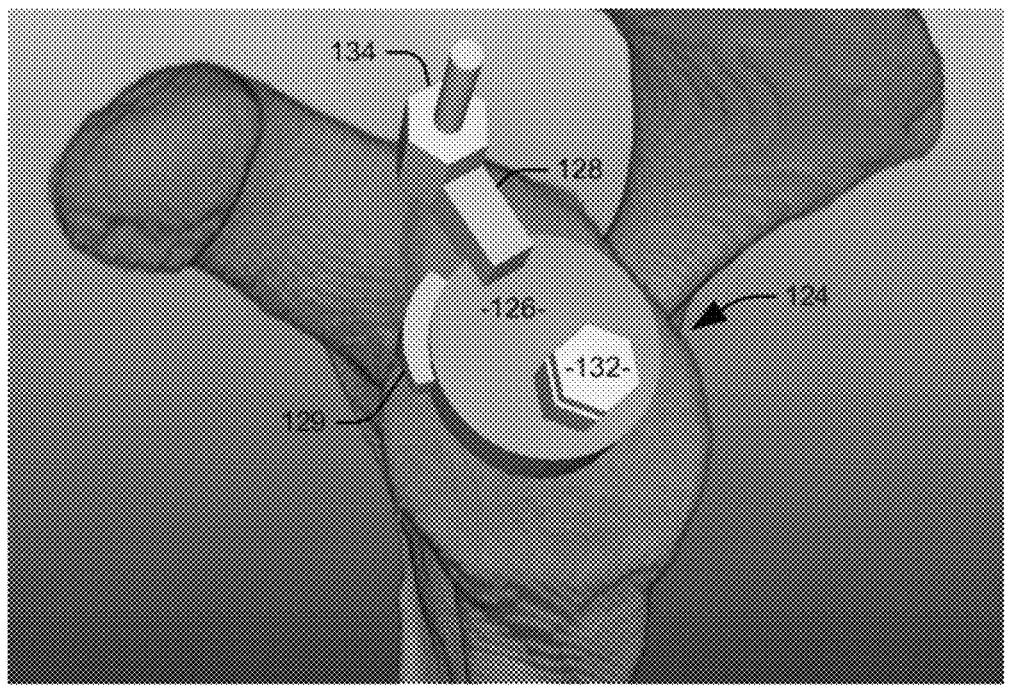
FIG. 14 illustrates the generic PSI model of FIGS. 12 and 13 positioned within the region of interest including attributes visible to a second user.

FIG. 14 illustrates the generic PSI model 124 of FIGS. 12 and 13 positioned within the region of interest. In the illustrated diagram, the generic PSI model is shown with the device model 102 of FIGS. 6 and 7, with only the attributes visible to a technician shown, including a center hex boss 132 and a guide pin hex boss 134. It will be appreciated, however, that the generic PSI model 124 has been configured such that the first wedge 128 is an elongated rectangular wedge extending to the guide pin boss 134, and the second wedge 129 is configured as a short pie-shaped wedge extending from the cylinder 126.

In general, the technician will position and configure the generic PSI model 124 to satisfy two criteria. To begin with, the generic PSI model 124 must serve as a bridge to connect the various components of an implant, including ancillary components associated with the implant. In the illustrated example, the generic PSI model 124, particularly the first wedge 128, is configured to join the center hex boss 132 and the guide pin hex boss 134. In addition, the generic PSI model 124 is configured to cover the relevant portion of the region of interest such that, after the modeling process is completed, the generic PSI model 124 will have a substantially unique complimentary surface to engage with a surface of the region of interest.

Once the generic PSI model 124 has been configured, one or more patient specific instrument models can be designed from the generic PSI model, and fabricated to serve as guides to the surgical procedure. The patient-specific instrument may be, for example, the type disclosed in co-pending U.S. patent application Ser. No. 13/282,509, filed Oct. 27, 2011 and titled "System and Method for Association of a Guiding Aid with a Patient Tissue", the entire contents of which are incorporated herein by reference.

FIGS. 15-22 illustrate the creation of a patient specific instrument model from a generic PSI model according to a script associated with a stock implant model such as that illustrated in FIGS. 6 and 7. One example of a script is provided herein as Table 3.

TABLE 3

```
// create glenoid PSI model
drill_holes = [GlenoidImplant/Center Hex/bore/bore shape] +
  [GlenoidImplant/Auxiliary Pin Assembly/?/rotation/Auxiliary
  Pin/bore shape];
hex_boss = [GlenoidImplant/Center Hex/hex model] +
  [GlenoidImplant/Auxiliary Pin Assembly/?/rotation/Auxiliary
  Hex/hex model];
$template = $blank + hex_boss;
$template = $template − drill_holes;
$template = $template − $surface;
$template = split( $template, largest );
```

Figure 15:
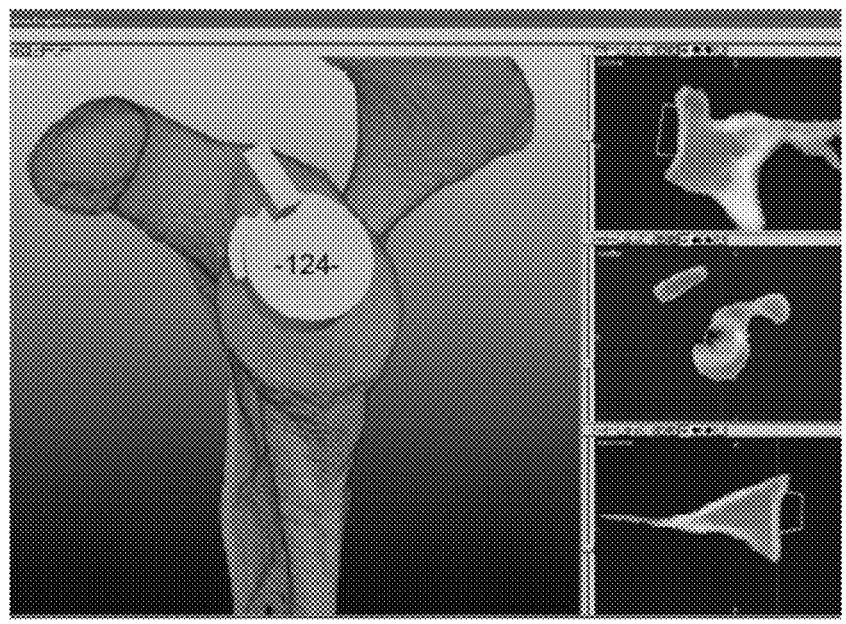
FIGS. 15 and 16 illustrate the generic PSI model before prior to the execution of a script for creating a final patient specific instrument.
Figure 16:
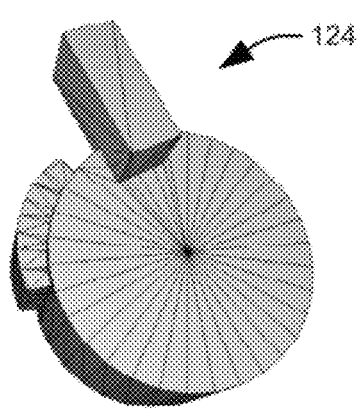

FIG. 15 illustrates the generic PSI model 124 positioned within the three-dimensional model of the region of interest. At this point, each of the implant model and the generic PSI model have been positioned and configured by the first and second users, and the script of Table 3 can be applied to form the final patient specific instrument model. Along with the generic PSI model itself, designated in the script as $blank, the script uses attributes of the implant model hidden from the surgeon, specifically the drill_holes object and the hex_nuts object. FIG. 16 illustrates the generic PSI model 124, prior to the execution of the script, as a mesh model.

Figure 17:
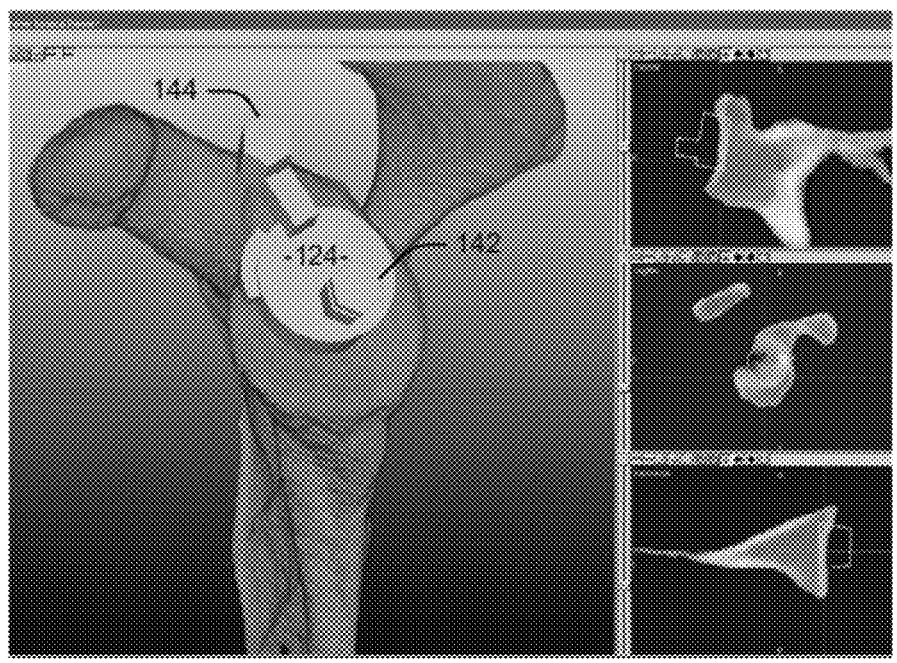
FIGS. 17 and 18 illustrate the generic PSI model of FIGS. 15 and 16 after a union with a model of two hex nuts.
Figure 18:
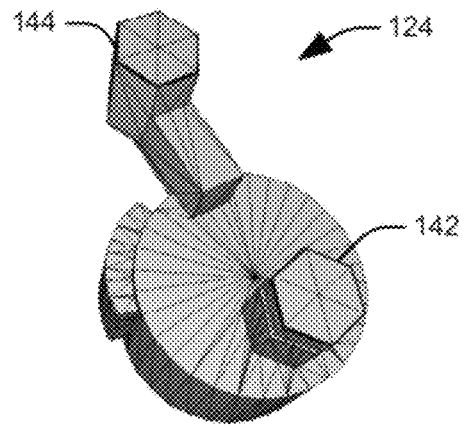
Figure 19:
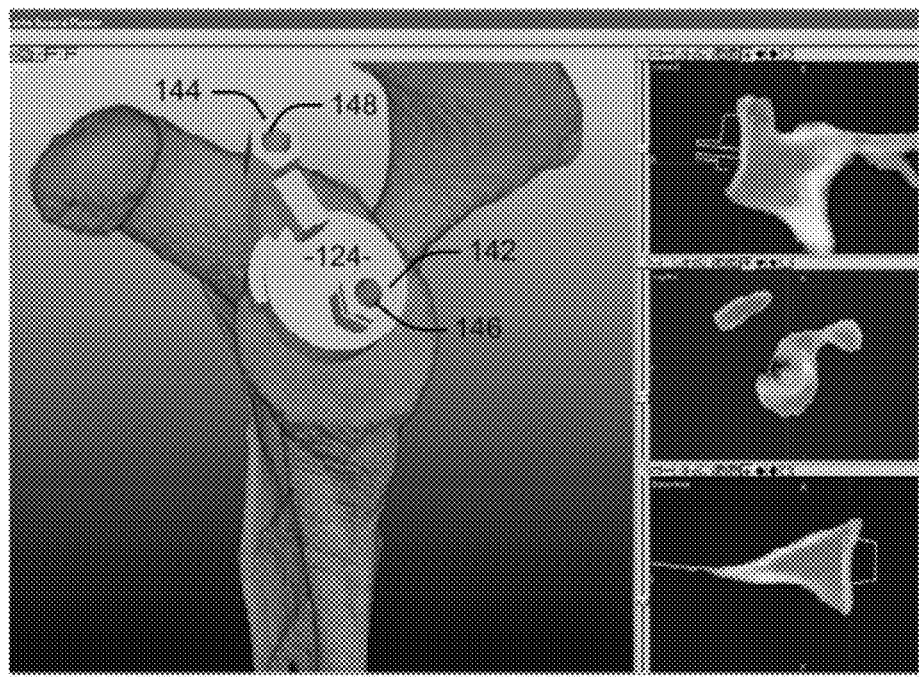
FIGS. 19 and 20 illustrate the generic PSI model of FIGS. 17 and 18 after the subtraction of two drill guides.
Figures 20, 22:
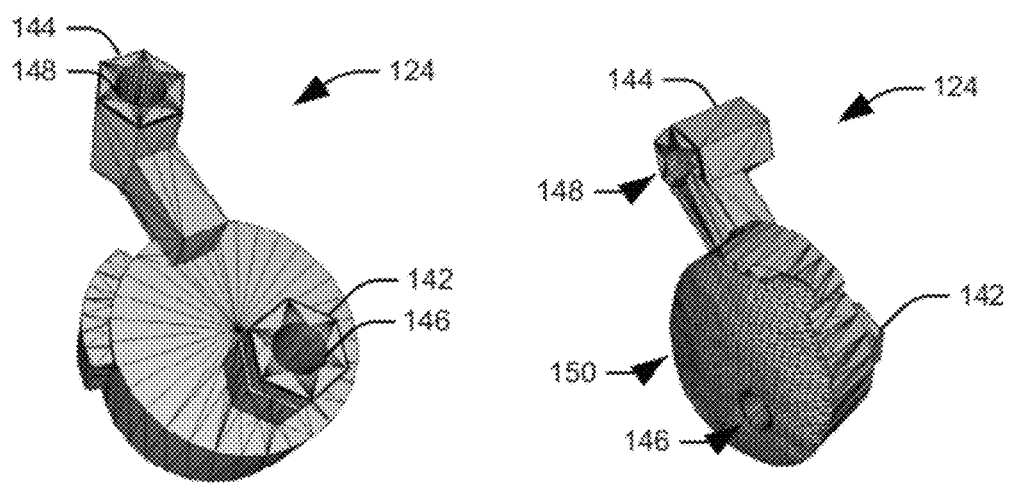
FIGS. 21 and 22 illustrate the generic PSI model of FIGS. 19 and 20 after the subtraction of a surface model from one surface of the generic PSI model.

FIGS. 17 and 18 illustrate the generic PSI model 124 of FIGS. 15 and 16 after execution of a union between the generic PSI model and the hex_nuts object. The union with the hex_nuts object adds a first hexagonal nut 142 associated with a center pin and a second hexagonal nut 144 associated with an auxiliary pin to the generic PSI model 124. FIGS. 19 and 20 illustrate the generic PSI model 124 of FIGS. 17 and 18 after subtraction of a drill_holes object from the generic PSI model. The subtraction provides a first drill guide 146 to facilitate placement of the center pin and a second drill guide 148 to facilitate placement of the auxiliary pin.

Figure 21:
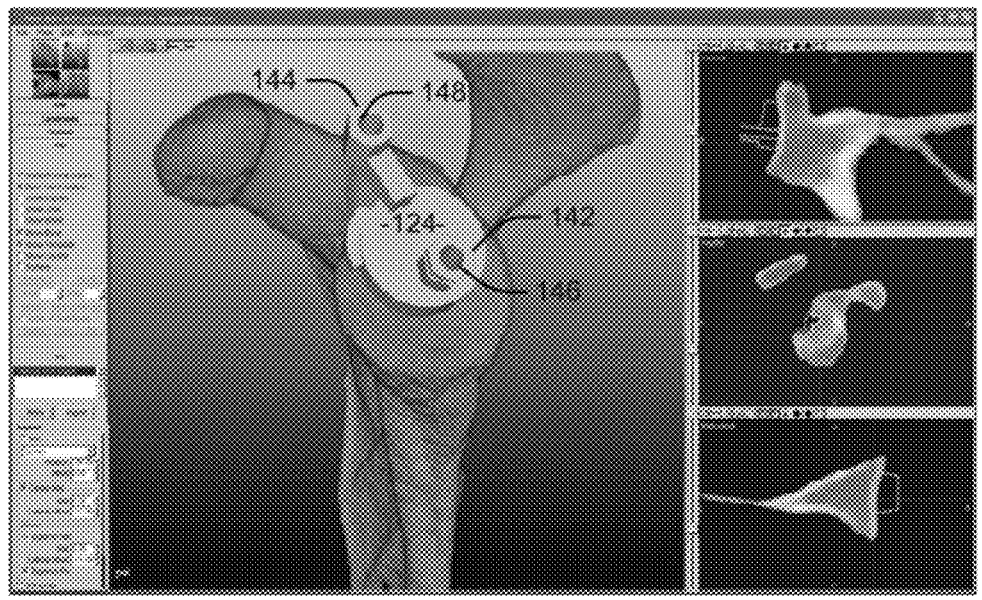

FIGS. 21 and 22 illustrate the generic PSI model 124 of FIGS. 19 and 20 after subtraction of a bone surface from the generic PSI model to create a final patient specific instrument model. The subtraction produces a contoured surface that will conform with the surface of the bone within the patient. It will be appreciated that this contoured surface can be used to guide the placement of a patient specific instrument made from the illustrated model, which, in turn, can guide the placement of the center pin and guide pin of a stock implant. Accordingly, the insertion of the stock implant can be performed with enhanced accuracy. A final instruction in the script executes a function that takes the template and keeps only the largest connected object. This eliminates any disjoint surfaces created via subtractions. The function cleans up the model by only keeping a largest portion (e.g., the portion with the most triangles).

Figure 23:
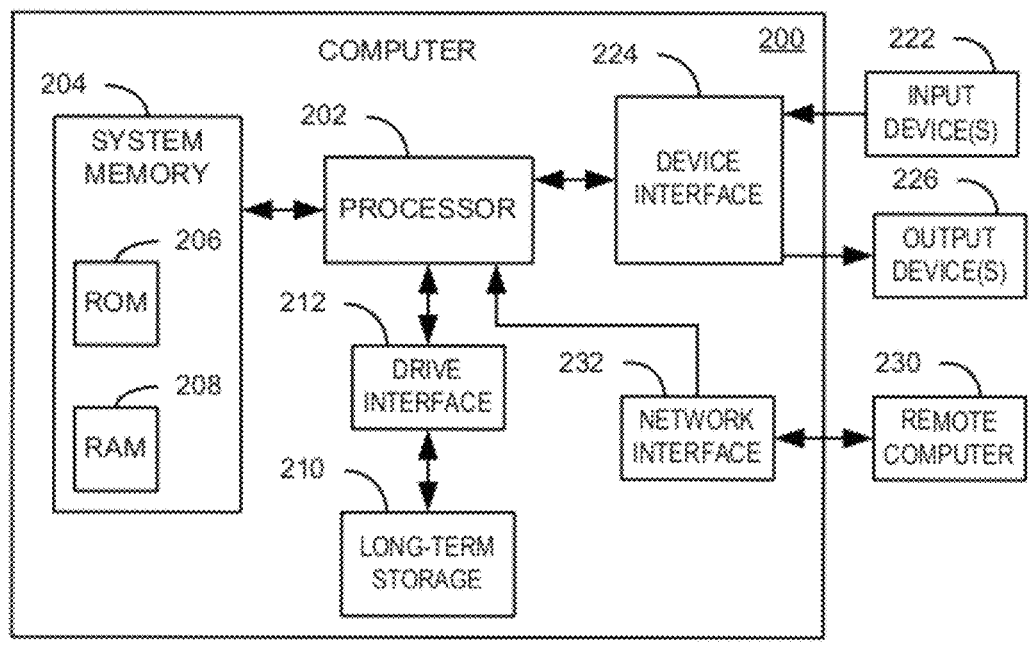
FIG. 23 is a schematic view of a computer system that can be employed to implement systems and methods described herein, such as based on computer executable instructions running on the computer system.

FIG. 23 illustrates a computer system 200 that can be employed to implement systems and methods described herein, such as based on computer executable instructions running on the computer system. The user may be permitted to preoperatively simulate the planned surgical procedure using the computer system 200 as desired. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 206 and random access memory (RAM) 208. A basic input/output system (BIOS) can reside in the ROM 206, generally containing the basic routines that help to transfer information between elements within the computer system 200, such as a reset or power-up.

The computer system 200 can include one or more types of long-term data storage 210, including a hard disk drive, a magnetic disk drive, (e.g., to read from or write to a removable disk), and an optical disk drive, (e.g., for reading a CD-ROM or DVD disk or to read from or write to other optical media). The long-term data storage 210 can be connected to the processor 202 by a drive interface 212. The long-term data storage 210 components provide nonvolatile storage of data, data structures, and computer-executable instructions for the computer system 200. A number of program modules may also be stored in one or more of the drives as well as in the RAM 208, including an operating system, one or more application programs, other program modules, and program data.

A user may enter commands and information into the computer system 200 through one or more input devices 222, such as a keyboard or a pointing device (e.g., a mouse). These and other input devices are often connected to the processor 202 through a device interface 224. For example, the input devices can be connected to the system bus by one or more a parallel port, a serial port or a universal serial bus (USB). One or more output device(s) 226, such as a visual display device or printer, can also be connected to the processor 202 via the device interface 224.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system are merely illustrative. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. A given patient-specific instrument may include a plurality of structures cooperatively forming the base body and temporarily or permanently attached together in such a manner as to permit relative motion (e.g., pivoting, sliding, or any other motion) therebetween. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. The system is described herein as being used to plan and/or simulate a surgical procedure of implanting one or more prosthetic structures into a patient's body, but also or instead could be used to plan and/or simulate any surgical procedure, regardless of whether a non-native component is left in the patient's body after the procedure. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

I claim:

1. A combination of a non-transitory computer readable medium storing machine readable instructions for fabricating a patient specific instrument (PSI) for use as a surgical guide for a surgical implant and of a model of the PSI in a digital format for use in fabricating the PSI, and the PSI, the combination comprising:

the machine readable instructions comprising:
a region modeling component configured to provide a three-dimensional model of a region of interest within a body from at least one imaging scan of the region of interest,
a surgical planning component configured to display a visible portion of a model of the implant and the three-dimensional model of the region of interest to a first user and allow the first user to select a preoperative surgical plan including a position of the implant within the three-dimensional model of the region of interest in a desired orientation, the implant having at least one hidden attribute that is not visible to the first user, the at least one hidden attribute of the implant being an implant extension configured to extend into a bone in the region of interest for maintaining the implant in the desired orientation relative to the region of interest, and
a PSI design component configured to prohibit alterations to the preoperative surgical plan selected by the first user, the PSI design component configured to display the at least one hidden attribute that is not visible to the first user, to generate at least one guide structure as extending from the implant extension and out of bone in the region of interest when the implant is in the desired orientation, the PSI design component configured to generate a model of the PSI incorporating at least one guide hole, the PSI design component configured to generate the at least one guide hole by subtracting the at least one guide structure from a generic PSI model, the PSI design component configured to display the at least one guide structure relative to the region of interest while excluding the visible portion of the implant;
the model of the PSI in a digital format for use in fabricating the PSI; and
the PSI fabricated from the model of the PSI in the digital format to implement the preoperative surgical plan, the PSI fabricated using data related to the model of the PSI in the digital format to control a manufacturing apparatus.

2. The combination of claim 1, each of the implant, the model of the region of interest, and the generic PSI model comprising a model, and the PSI design component being configured to provide the patient specific instrument model as a series of geometry processing operations on the implant, the model of the region of interest, and the generic PSI model.

3. The combination of claim 1, each of the implant and the generic PSI model comprising a model and the at least one hidden attribute comprising an extension on the implant, the PSI design component being configured to provide the patient specific instrument model as a series of geometry processing operations on the at least one hidden attribute and the generic PSI model.

4. The combination of claim 1, wherein the PSI design component prohibits displacement of the guide structure extending from the implant extension.

5. The combination of claim 1, the PSI design component further configured to select a portion of a surface within the region of interest and extrude the surface in a determined direction to provide the generic PSI model.

6. The combination of claim 1, wherein the region of interest is a shoulder joint and the region modeling component is configured to provide a three-dimensional model of at least one bone within the shoulder joint.

7. The combination of claim 1, wherein the region modeling component is configured to modify the three-dimensional model of the region of interest to eliminate any underhanging features on a portion of the three-dimensional model of the region of interest representing a bone.

8. The combination of claim 1, wherein the at least one hidden attribute comprises a first attribute that is visible to a second user.

9. The combination of claim 8, wherein the at least one hidden attribute comprises a second attribute that is not visible to either of the first user and the second user.

10. A computer-implemented method for fabricating a patient specific instrument (PSI) for use as a surgical guide for a surgical implant, comprising:

scanning a region of interest within a body of a patient to provide a three-dimensional model of the region of interest;

allowing a first user to select a preoperative surgical plan by positioning a model of the implant to a desired orientation with respect to the three-dimensional model of the region of interest via a graphical user interface by displaying a visible portion of the implant relative to the three-dimensional model of the region of interest, the implant having at least one hidden attribute that is not visible to the first user, the at least one hidden attribute of the implant being an implant extension configured to extend into a bone in the region of interest configured for maintaining the implant in the desired orientation relative to the region of interest;

prohibiting alterations by a second user to the preoperative surgical plan selected by the first user, displaying to the second user the at least one hidden attribute that is not visible to the first user, a model of the PSI relative to the region of interest while excluding the visible portion of the implant, for the second user to alter parameters of the model of the PSI;

generating the model of the PSI incorporating at least one guide hole, the at least one guide hole resulting from a subtraction of a guide structure from a generic PSI model, the guide structure configured to extend from the implant extension and out of bone in the region of interest when the implant is in the desired orientation; and fabricating the PSI according to the model of the PSI configured for implementing the preoperative surgical plan, fabricating the PSI comprises using data related to the model of the PSI in the digital format to control a manufacturing apparatus.

11. The method of claim 10, wherein generating a model of the PSI from a generic PSI model comprises performing a series of geometry processing operations on the implant, an at least one extension of the implant, the three-dimensional model of the region of interest, and the generic PSI model.

12. The method of claim 11, wherein performing the series of geometry processing operations comprises subtracting a portion of intersection between the three-dimensional model of the region of interest and the generic PSI model from the generic PSI model such that a first surface of the generic PSI model is contoured to a portion of a surface of the three-dimensional model of the region of interest.

13. The method of claim 11, further comprising prohibiting displacement of the guide structure extending from the implant extension after allowing the first user to position the model of the implant.

14. The method of claim 11, wherein performing the series of geometry processing operations comprises taking the union of an extension of the at least one extension and the generic PSI model as to add the at least one guide structure to the generic PSI model.

15. The method of claim 11, applying a parameterized transform operation to at least a portion of the generic PSI model to produce a desired deformation in the generic PSI model.

16. The method of claim 10, further comprising generating one of the model of a selected implant and the generic PSI model as a specific instance, represented by an appropriate set of parameters, of an implicitly defined model.

17. The method of claim 10, further comprising modifying the three-dimensional model of the region of interest to eliminate features on a portion of the three-dimensional model of the region of interest expected to interfere with the engagement of the model with the region of interest.

18. The method of claim 10, further comprising allowing a second user to configure the generic PSI model to alter at least one of the size and the shape of the generic PSI model.

19. The method of claim 10, further comprising allowing a second user to configure the model of the selected implant to alter one of the size and position of a first extension of the implant.

20. The method of claim 10, wherein generating a patient specific instrument model from a generic PSI model comprises executing a script in an associated script language.

21. A system for fabricating a patient specific instrument (PSI) for use as a surgical guide for a surgical implant, the system comprising a non-transitory computer readable medium storing machine readable instructions for performing a method comprising the steps of:

allowing a first user to select a preoperative surgical plan by positioning a model of the implant in a desired orientation relative to a three-dimensional model of a region of interest by displaying a visible portion of the implant relative to the three-dimensional model of the region of interest, the implant having at least one hidden attribute that is not visible to the first user, the at least one hidden attribute of the implant being an implant extension configured to extend into a bone in the region of interest for maintaining the implant in the desired orientation relative to the region of interest;

allowing a second user to alter a first attribute of the implant by displaying the at least one hidden attribute that is not visible to the first user, and at least one guide structure relative to the region of interest to the second user, while excluding the visible portion of the implant from being viewed by the second user, the at least one guide structure extending from the implant extension and out of bone in the region of interest when the implant is in the desired orientation;

concurrently prohibiting alterations by the second user to the preoperative surgical plan selected by the first user, generating a model of the PSI from a generic PSI model according to the preoperative surgical plan of the implant by the first user, the alteration of the first attribute by the second user, the model of the PSI incorporating at least one guide hole, the at least one guide hole resulting from a subtraction of the guide structure extending from the implant extension from the generic PSI model;

outputting the model of the PSI in a digital format for use in fabricating the PSI;

fabricating the PSI using data related to the model of the PSI in the digital format to control a manufacturing apparatus; and a processor configured to execute the machine readable instructions.

22. The non-transitory computer readable medium of claim 1, wherein the at least one hidden attribute of the model of the implant is not present in the surgical implant.

23. The system of claim 21, further comprising prohibiting displacement of the guide structure extending from the implant extension in the desired orientation of the model of the implant after allowing the first user to position the model of the implant in the desired orientation.

24. The non-transitory computer readable medium of claim 1, wherein the PSI is fabricated using at least one of selective laser sintering, fused deposition modeling, stereolithography, laminated object manufacturing, electron beam melting, three-dimensional printing, contour milling and computer numeric control.

* * * * *